United States Patent [19]
Lichter et al.

[11] Patent Number: 5,827,179
[45] Date of Patent: Oct. 27, 1998

[54] PERSONAL COMPUTER CARD FOR COLLECTION FOR REAL-TIME BIOLOGICAL DATA

[75] Inventors: Patrick A. Lichter, Plymouth; Spencer J. Lien, Medina, both of Minn.

[73] Assignee: QRS Diagnostic, LLC, Plymouth, Minn.

[21] Appl. No.: 810,632

[22] Filed: Feb. 28, 1997

[51] Int. Cl.[6] ...................................................... A61B 5/00
[52] U.S. Cl. ........................ 600/300; 600/538; 600/481; 128/920
[58] Field of Search .................................... 600/301, 300, 600/529, 537, 538, 539, 540, 309, 481; 128/903, 904, 920

[56] References Cited

U.S. PATENT DOCUMENTS

| | | |
|---|---|---|
| 3,921,147 | 11/1975 | Fuhr et al. . |
| 4,356,475 | 10/1982 | Neumann et al. ...................... 340/521 |
| 4,905,709 | 3/1990 | Bieganski et al. . |
| 5,305,202 | 4/1994 | Gallant et al. . |
| 5,307,263 | 4/1994 | Brown ..................................... 600/301 |
| 5,501,231 | 3/1996 | Kaish . |
| 5,518,002 | 5/1996 | Wolf et al. . |
| 5,549,115 | 8/1996 | Morgan et al. . |
| 5,562,101 | 10/1996 | Hankinson et al. . |
| 5,564,432 | 10/1996 | Thomson . |
| 5,623,925 | 4/1997 | Swenson et al. ....................... 600/301 |
| 5,687,717 | 11/1997 | Halpern et al. ......................... 128/903 |
| 5,701,894 | 12/1997 | Cherry et al. .......................... 128/904 |

OTHER PUBLICATIONS

Advance for Respiratory Managers Magazine, Advertisment Now You Can Enjoy The Benefits Of Spirometry Testing, QRS, Aug. 1996.
Technology Providers, Microsoft Press Release—Comdex Trade Show in Las Vegas, Nov. 1996.

*Primary Examiner*—Jennifer Bahr
*Assistant Examiner*—Eric F. Winakur
*Attorney, Agent, or Firm*—Frank J. Uxa; Kenton R. Mullins

[57] ABSTRACT

A real-time biological data processing PC card is very lightweight, cost effective, and portable. The real-time biological data processing PC card is capable of converting a host personal computer system into a powerful diagnostic instrument. Each real-time biological data processing PC card is adapted to input and process biological data from one or more biological data sensors, and is interchangeable with other real-time biological data processing PC cards. A practitioner having three different real-time biological data processing PC cards, for example, each one corresponding to a different biological data collection device, effectively carries three full-sized, powerful diagnostic instruments. The full resources of a host personal computer can be utilized and converted into a powerful diagnostic instrument, for each biological data collection device, by the insertion of one of the real-time biological data processing PC cards.

26 Claims, 5 Drawing Sheets

PERSONAL COMPUTER CARD FOR COLLECTION FOR REAL-TIME BIOLOGICAL DATA

BACKGROUND OF THE INVENTION

1. Field of the Invention

The present invention relates generally to personal computer (PC) cards and, more particularly, to PC cards for use in combination with personal computers for collecting biological data on a real-time basis.

2. Description of Related Art

The United States health care system is currently in the midst of a transformation away from specialized medicine toward a more cost-conscious, primary-care oriented system. Devices having cost-effective means for diagnosing and monitoring patients are expected to gain prominence in the market place. Many current data acquisition devices exist in the medical industry, but few, if any, of these devices are economical, extremely lightweight and portable, accurate, versatile, and interchangeable with other biological data collection devices.

One prior art device, manufactured by the assignee of the present application, incorporates a diagnostic box which is adapted to interface with a serial port of a personal computer. This diagnostic box is manufactured with a relatively expensive housing, having a size approximately equal to that of a book, an alternating current (AC) cord and power adapter, a serial port cable, a microprocessor, and other hardware elements.

The diagnostic box allows a user to perform real-time spirometry operations, while harnessing the PC computer's display, keyboard, printer, and other items. The PC computer display instructs the user with selectable patient incentives, and user-customized reports can be generated. The display of the personal computer can be configured to display volume-versus-time and flow-versus-volume curves. Additionally, parameters such as maximum exhale volume, maximum inhale volume and maximum flow rate can be computed and displayed on the personal computer display.

Data acquisition cards have existed in the prior art for transferring electrical signals from a data sensor through the data acquisition card and into a personal computer. These data acquisitions cards have been configured into Personal Computer Memory Card International Association (PCMCIA) cards.

Prior art data acquisition cards are often configured to measure potential signals ranging from zero to ten volts, and are often configured with twelve bit accuracy. A typical prior art data acquisition card may comprise a 30 pin connector and a cable, which is connected to a connector board. The connector board allows a user to hook up various signals thereto. In addition to the relatively high-voltage signal range (zero to ten volts), low-accuracy (e.g. twelve bits), extra hardware (30 pin connector, cable, and a connector board), and additional optional hardware, these prior art data acquisition cards are configured with a plurality of inputs and outputs and, further, are not adapted to convert a personal computer into a powerful biological data signal collecting, processing, and monitoring system.

Prior art data acquisition cards are not adapted for performing spirometry collection and analysis, since these cards are not equipped with pressure transducers for converting pressure signals into electrical signals. Even if these prior art data acquisition cards were equipped with pressure transducers, the cards would not be equipped with high-precision low-voltage signal collection and conditioning circuitry. A prior art data acquisition card, additionally, would not be suitable for other biological data collection and processing purposes, such as Electrocardiography (ECG) biological data collection, since these prior art data acquisition cards are not equipped with any insulating means for insulating a patient from potential shock, which may be delivered from the data acquisition card to the patient.

Another prior art device is disclosed in U.S. Pat. No. 5,549,115 to Morgan et al. The Morgan et al. patent generally discloses a PCMCIA format card which is adapted to perform as a data storage device, similarly to a floppy disc storage device. The PCMCIA format cart of Morgan et al. is equipped with a real-time clock for providing time and date data to the host system, in order to synchronize the host system time with the time of which the data was actually acquired. The PCMCIA format card of Morgan et al. does not provide any means for real-time data collection and processing and, accordingly, is not suitable for converting a host PC computer into a real-time biological data signal collection, processing, and monitoring system. The system of the Morgan et al. patent requires a separate dedicated computer device for acquiring the data, and a separate personal computer device for processing the data at a later time.

U.S. Pat. No. 5,546,432 to Thomson discloses a spirometer which includes control electronics located remotely from a hand-held housing. Communication between the hand-held housing, which includes an analog-to-digital (A/D) converter and an amplifier, occurs through a cable. A dedicated microprocessor including a simple keyboard structured and adapted specifically to control the operation of a spirometer is included in the Thomson device. The handle-shaped housing of the Thomson patent is quite different from a PC card.

A need exists in the prior art for real-time biological data signal collecting, processing, and monitoring systems, which are extremely lightweight and portable. The prior art has not introduced any cost-effective PC card, which is adapted to convert a host personal computer into any of a variety of real-time data collecting and processing systems.

SUMMARY OF THE INVENTION

The real-time biological data processing PC card of the present invention is very lightweight, cost effective, and portable. The real-time biological data processing PC card of the present invention is capable of converting a host personal computer system into a powerful diagnostic instrument. Each real-time biological data processing PC card is adapted to input and process biological data from one or more biological data sensors, and is interchangeable with other real-time biological data processing PC cards. A practitioner having three different real-time biological data processing PC cards, each one corresponding to a different biological data collection device, effectively carries three full-sized, powerful diagnostic instruments. The full resources of a host personal computer may be utilized and converted into a powerful diagnostic instrument, for each biological data collection device, by the insertion of one of the real-time biological data processing PC cards.

A portable computer card for collecting biological data, according to the present invention, includes a pressure transducer adapted to receive an air pressure from an air tube and to convert the air pressure into an electrical signal. The portable computer card includes an analog-to-digital converter adapted to receive and digitize the electrical signal, and a portable computer card interface adapted to provide an interface between the portable computer card and a host microprocessor system. The portable computer card interface may comprise a PCMCIA card interface. An amplifier, which is adapted to receive and amplify the electrical signal from the pressure transducer, is disposed between the pressure transducer and the analog-to-digital converter. The amplified electrical signal is related to the air pressure. The portable computer card further includes a housing, which is adapted for holding the pressure transducer, the amplifier, the analog-to-digital converter, and the portable computer card interface. A pressure input port is disposed on the housing. This pressure input port is in fluid communication with the pressure transducer and is adapted to receive an air pressure from an air tube. The portable computer card further includes a flexible air passageway, which is integrally connected to the housing, and which is adapted to supply an air pressure to the pressure input port.

According to still another aspect of the present invention, a portable biological data collection device includes a portable computer card housing, a biological data receiver, signal conditioning circuitry, and a portable computer card interface. The biological data receiver is adapted to receive biological data and to output the biological data, and the signal conditioning circuitry is adapted to receive the biological data from the biological data receiver and to convert the biological data into digitized biological data. The portable computer card interface is disposed within the portable computer card housing, and is adapted to communicate with a host computer to relay the digitized biological data to the host computer on a real-time basis as the biological data is converted by the signal conditioning circuitry.

The biological data receiver can be adapted to receive biological data from a pulse oximetry sensor, which is located externally of the portable biological data collection device. The biological data receiver can further be adapted to receive biological data from an ECG sensor. The biological data sensor is adapted to output low-amplitude signals on an order of one millivolt. The digitized data from the analog-to-digital converter preferably has a resolution greater than 12 bits and, preferably, has a resolution of 16 bits. The biological data sensor may further include a spirometer air tube.

According to another aspect of the present invention, a host computer is configurable among a plurality of biological data collection device modes. The host computer includes a portable computer card slot adapted to receive a portable computer card therein, a portable computer card interface adapted to communicate with a portable computer card inserted into the portable computer card slot, a microprocessor, a data bus, and input means for receiving designation data from a portable computer card within the portable computer card slot. The portable computer card interface is adapted to receive digitized biological data from a portable computer card inserted into the portable computer card slot, and the input means is operatively connected to the microprocessor. The designation data is indicative of a type of digitized biological data from a portable computer card inserted into the portable computer card slot. The designation data may comprise either a first identifier for indicating that the digitized biological data should be interpreted by the microprocessor as spirometer-pressure data or a second identifier indicating that the digitized biological data should be interpreted by the microprocessor as pulse oximetry electrical data. The host computer includes configuration means for configuring the host computer into a real-time spirometer-pressure data collecting and analyzing device upon receipt of the first identifier, and for configuring the host computer into a real-time pulse oximetry electrical data collecting and analyzing device upon receipt of the second identifier. The host computer may also be configured into an ECG data collection device mode, upon receipt of a third identifier from the input means. Additionally, the host computer may be configured among various other biological data collection device modes, upon receipt of additional identifiers.

According to yet another aspect of the present invention, a combination of a plurality of interchangeable biological data portable computer cards includes a spirometer portable computer card and a pulse oximetry portable computer card. The spirometer portable computer card and the pulse oximetry portable computer card are both insertable into a personal computer system, and are interchangeable. The spirometer portable computer card is adapted to convert the host computer into a spirometer data collecting and analyzing device, and the pulse oximetry portable computer card is adapted to convert the host computer into a pulse oximetry data collecting and analyzing device. The combination of interchangeable biological data portable computer cards may further include an ECG portable card, as well as other computer cards, each being adapted to convert the host personal computer into a different type of biological data collecting and analyzing device.

According to another aspect of the present invention, a portable computer card for delivering biological data to a host computer includes a portable computer card housing, at least one conductor connected to the portable computer card housing, an amplifier operatively connected to the at least one conductor, a power source operatively connected to the amplifier, and insulating means for providing electrical insulation between the power source and the conductor. The conductor is adapted to collect biological data from a patient, and the amplifier is adapted to receive the biological data and to output an amplified signal. The insulating means may comprise an optical translator, and can be positioned between the conductor and the amplifier. The portable computer card further includes an analog-to-digital converter for digitizing the amplified signal, and a portable computer card interface for providing a communication link between the portable computer card and a host personal computer system. The portable computer card interface is adapted to relay the digitized amplified signal to the host computer on a real-time basis, as biological data is collected from a patient. The power source comprises a conductor, which is adapted for receiving power from the host personal computer.

The present invention, together with additional features and advantages thereof, may best be understood by reference to the following description taken in connection with the accompanying illustrative drawings.

BRIEF DESCRIPTION OF THE DRAWINGS

FIG. 1a illustrates an end view of the real-time biological data processing PC card of FIG. 1, taken from the direction of the line 1a—1a;

DETAILED DESCRIPTION OF THE PRESENTLY PREFERRED EMBODIMENTS

Figures 1, 1B:
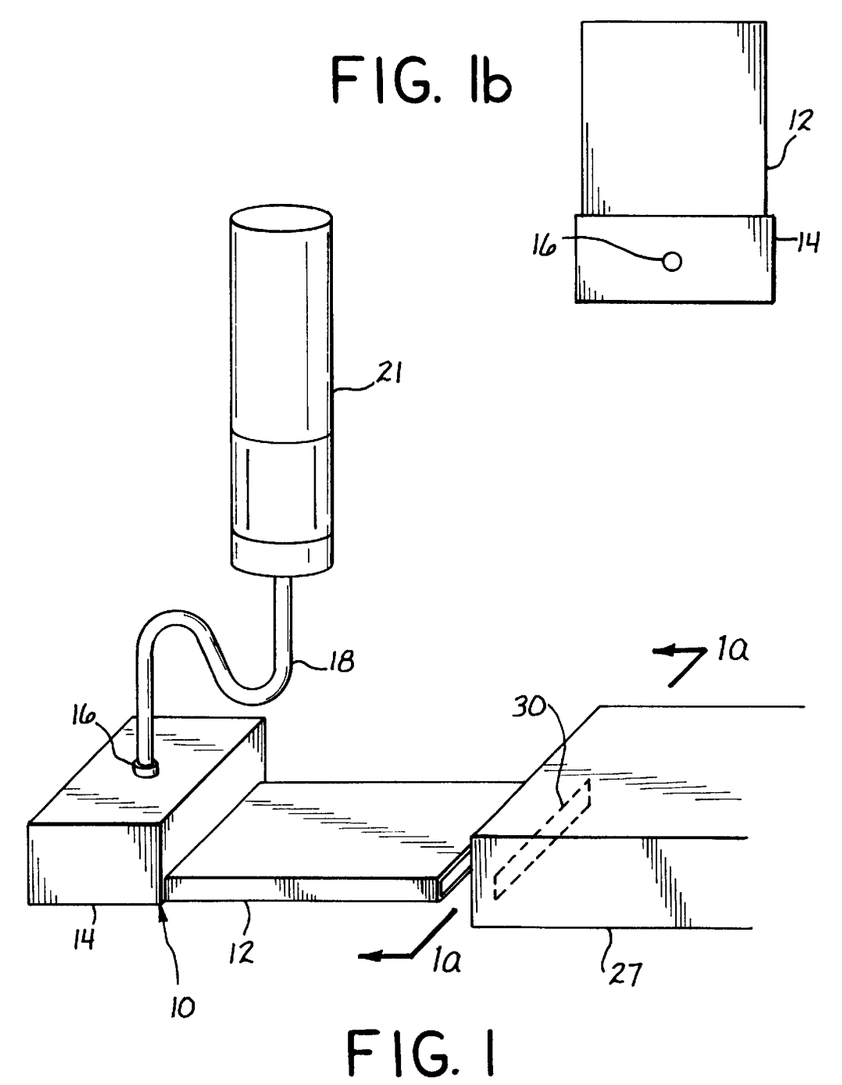
FIG. 1 illustrates a real-time biological data processing PC card according to the present invention.
FIG. 1b illustrates a top planar view of the real-time biological data processing PC card, without the air tube connection.

Turning to FIG. 1, a real-time biological data processing PC card 10 is illustrated having a Personal Computer Memory Card International Association (PCMCIA) format housing 12 and a pressure transducer housing 14. The pressure transducer housing 14 preferably comprises a pressure input port 16, which is adapted to removably accommodate a flexible air passageway 18. A disposable spirometry mouthpiece 21 is attached to one end of the flexible air passageway 18, and a connector is attached to the other end of the flexible air passageway 18. As presently embodied, the connector comprises a truncated, conical shape which is adapted for matingly fitting within the pressure input port 16. After a user breaths into the disposable spirometry mouthpiece 21, the flexible air passageway 18 and the disposable spirometry mouthpiece 21 may be removed from the pressure input port 16, and discarded.

The PCMCIA format housing 12 of the real-time biological data processing PC card 10 is preferably configured to conform with PCMCIA dimensional standards. As presently preferred, the PCMCIA format housing has a width of approximately 2.95 inches. The PCMCIA format housing 12 preferably comprises a length of approximately 3.40 inches. The pressure transducer housing 14, according to the presently preferred embodiment, has dimensions which are larger than PCMCIA conventions permit. As presently embodied, the pressure transducer housing 14 comprises a height of approximately 1 inch. These enlarged dimensions of the pressure transducer housing 14 facilitate placement of biological sensor circuitry, such as, for example, a pressure transducer.

Figure 1A:
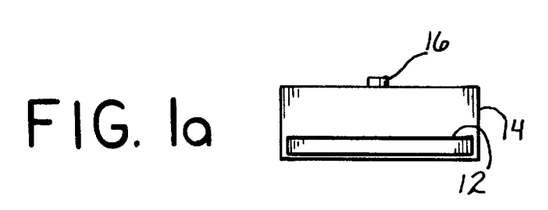

FIG. 1a illustrates an end view of the real-time biological data processing PC card 10, taken from a view along the line 1a—1a of FIG. 1, and FIG. 1b illustrates a top-planar view of the real-time biological data processing PC card 10. A host personal computer 27 comprises a PCMCIA format slot 30, which is sized and dimensioned according to PCMCIA dimensional standards, in order to facilitate insertion of the PCMCIA format housing 12 therein.

Figure 2:
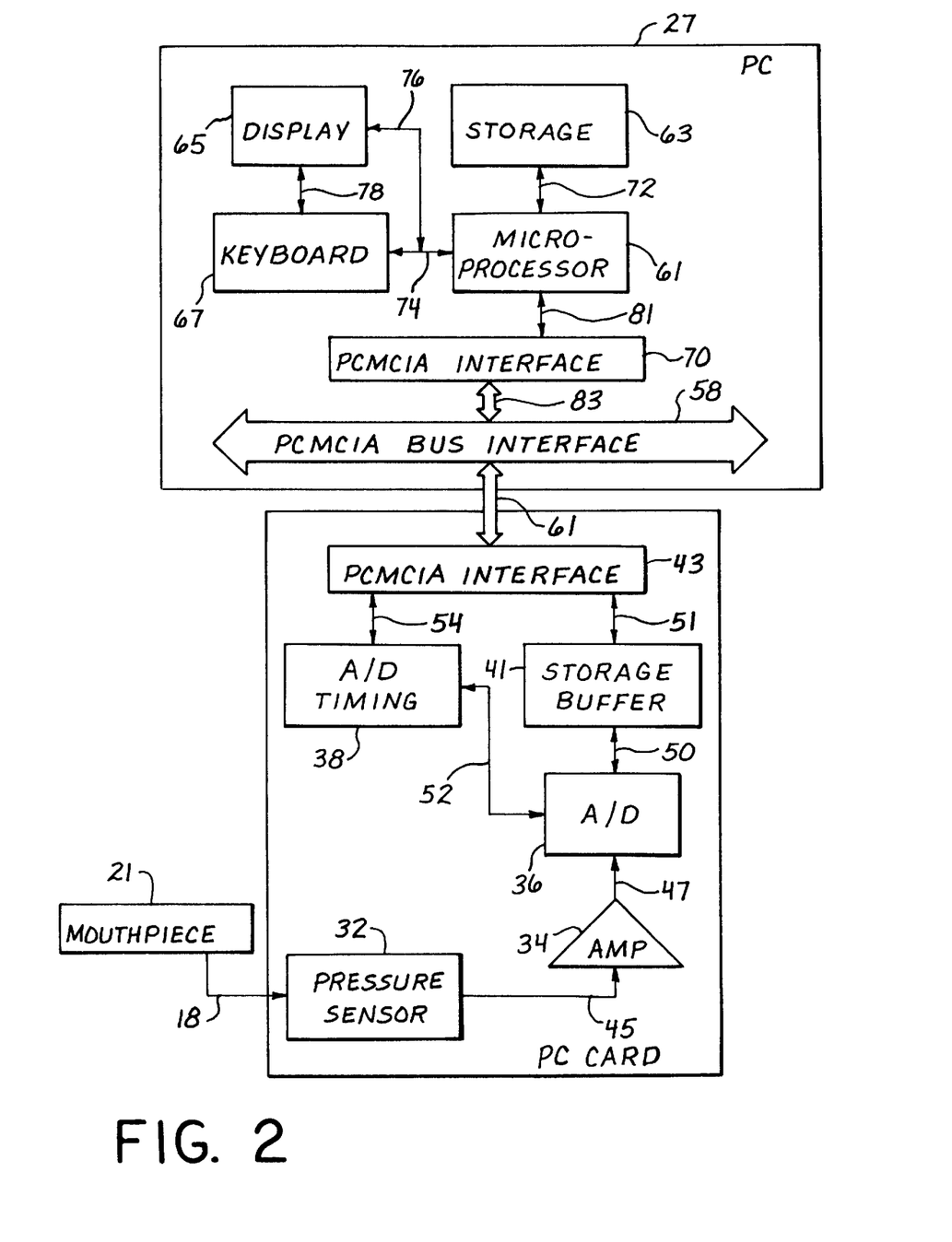
FIG. 2 illustrates a schematic block diagram of the circuitry of the real-time biological data processing PC card and a host personal computer system, according to the present invention.

FIG. 2 illustrates a schematic block diagram of components associated with the real-time biological data processing PC card 10 and the host personal computer 27. The real-time biological data processing PC card 10 comprises a pressure sensor 32, an amplifier 34, an analog-to-digital converter 36, an analog-to-digital timing circuit 38, a storage buffer 41, and a PCMCIA interface 43. The flexible air passageway 18 connects the disposable spirometry mouthpiece 21 to the pressure sensor 32, and a conductor path 45 connects the pressure sensor 32 to the amplifier 34. The amplifier 34 is connected to the analog-to-digital converter 36 via a conductor path 47, and the analog-to-digital converter 36 is connected to the storage buffer 41 via a conductor path 50. A conductor path 52 connects the analog-to-digital converter 36 to the analog-to-digital timing circuit 38, and a conductor path 54 connects the analog-to-digital timing circuit 38 to the PCMCIA interface 43. The storage buffer 41 is connected to the PCMCIA interface 43 via a conductor path 51. Upon insertion of the real-time biological data processing PC card 10 into the PCMCIA format slot 30, the PCMCIA interface 43 is connected to a PCMCIA bus interface 58 via a bus 61.

The host personal computer 27 comprises a microprocessor 61, a storage 63, a display 65, a keyboard 67, and a PCMCIA interface 70. The host personal computer 27, of course, may comprise other components which are not shown in FIG. 2. The microprocessor 61 is connected to the storage 63 via a bus 72, and is connected to the keyboard 67 via a bus 74. A bus 76 connects the display 65 to the bus 74, and a bus 78 connects the display 65 to the keyboard 67. The microprocessor 61 is connected to the PCMCIA interface 70 via a bus 81, and the PCMCIA interface 70 is connected to the PCMCIA bus interface 58 via a bus 83.

When the real-time biological data processing PC card 10 and the host personal computer 27 are configured as shown in FIG. 2, communication between the devices 10 and 27 can occur via standardized PCMCIA protocols. The PCMCIA Developer's Guide—2nd Edition, published by Sycard Technology in 1994, the contents of which are expressly incorporated herein by reference, discloses information on PCMCIA conventions and protocols.

Although the embodiment of FIG. 2 is shown comprising a pressure sensor 32 and a disposable spirometry mouthpiece 21, any biological data sensor and/or associated components may be incorporated into the real-time biological data processing PC card 10. As presently preferred, each biological data sensor, having a different format of biological data, is configured in a separate real-time biological data processing PC card. The various real-time biological data processing PC cards are interchangeable, to thereby configure the host personal computer 27 into various real-time biological data collecting and processing modes. Alternatively, a single real-time biological data processing PC card 10 may be configured to accommodate one or more different types of biological data sensors. According to the present invention, various interchangeable real-time biological data processing PC cards can configure the host personal computer 27 into various collecting, processing, and monitoring modes, including spirometry, electrocardiography (including resting, 24-hour, stress testing, signal averaging, event ECG, and heart-rate variability), blood pressure, body temperature, electroencepholograhy (EEG), echocardiography, Doppler, pulse oximetry (SPO2), sleep analysis, tcPO2, tcPCO2, nitrogen dioxide, capnography, respiratory rate, pulse rate, polysomnography, carbon monoxide, gastroesophageal pH, hydrogen, nitric oxide, body composition, glucometer, audiometry, plethysmograph, weight, electromyography, urometry, and tympanometry, for example. Other biological data may also be collected and processed by the host personal computer 27, after being configured by a corresponding real-time biological data processing PC card.

The real-time biological data processing PC card 10 shown in FIG. 2, which is adapted for configuring the host personal computer 27 for spirometry procedures, receives a pressure signal from the mouth piece 21. The pressure sensor 32, which preferably comprises a pressure transducer, converts the pressure signal into an electrical signal, which is amplified by the amplifier 34. The analog-to-digital converter 36, which is timed by the analog-to-digital timing circuit 38, receives the amplified biological data from the amplifier 34, and digitizes the biological data. The analog-to-digital timing circuit 38 provides a timing signal, which facilitates sampling of the amplified biological data on the conductor path 47. This digitized biological data is output onto the conductor path 50. The storage buffer 41 receives the digitized biological data, and outputs this digitized biological data onto a conductor path 51, where the digitized biological data is made available to the PCMCIA interface 43. The storage buffer 41 preferably comprises a first in first out (FIFO) buffer, and may be omitted for simple configurations where buffering capabilities are not needed. The real-time biological data processing PC card 10 further comprises control circuitry, and the PCMCIA interface 43 preferably comprises input output (I/O) interface glue logic and an input output connector.

Upon insertion of the real-time biological data processing PC card 10 into the PCMCIA format slot 30 of the host computer 27, the microprocessor 61, the PCMCIA interface 70 of the host computer 27, and the PCMCIA interface 43 of the real-time biological data processing PC card 10 begin communicating via established PCMCIA format conventions. The microprocessor 61 determines the type of real-time biological data processing PC card which has been inserted into the PCMCIA format slot 30. In the illustrated case of FIG. 2, designation data from the PCMCIA interface 43 indicates to the microprocessor 61 that a spirometry-type real-time biological data processing PC card 10 has been inserted. Designation data from the PCMCIA interface 43 may, alternatively, identify the real-time biological data processing PC card 10 as being adapted for relaying oximetry, ECG, or other biological data to the host personal computer 27. As an alternative to, or in addition to, the illustrated embodiment of FIG. 2, a user may input designation data via the keyboard 67 or the display 65, indicating the type of real-time biological data processing PC card 10 which has been inserted into the PCMCIA format slot 30 of the host personal computer 27.

After the host personal computer 27 has "set up" the real-time biological data processing PC card 10, the host personal computer 27 prompts, via the display 65, the user to begin the spirometry test. As presently embodied, multi-media devices, such as entertaining displays and sounds, are implemented by the host personal computer 27 in order to educate the patient on how to perform the biological data test. The display 65 prompts the patient to begin the test, and coaches the patient during the test with, for example, entertaining incentives. This multi-media instructional system is configured to assist patients, especially in home disease management situations, helping asthmatics and cystic fibrosis patients, for example, comply with testing protocols. Additionally, the system of the present invention may reduce the need for skilled human interaction in order to achieve successful administration of the biological data tests.

The biological data from the pressure sensor 32, after being processed by the amplifier 34 and the analog-to-digital converter 36, is preferably immediately transferred from the PCMCIA interface 43 of the real-time biological data processing PC card 10 to the PCMCIA interface 70 of the host personal computer 27. The host personal computer 27, having received designation data indicating that the real-time biological data processing PC card 10 is a spirometry real-time biological data processing PC card, is configured to function as a complete spirometry data collecting, processing, and monitoring device. For example, a volume-versus-time wave form or a flow-versus-volume curve may be displayed on the display 65, indicating the real-time biological data received by the pressure sensor 32. A number of other parameters, such as maximum exhale volume, maximum inhale volume, and maximum flow rate, to name a few, may also be shown on the display 65 of the host personal computer 27. This data also may be compiled and printed in a variety of analytical and comparative formats.

Figure 3:
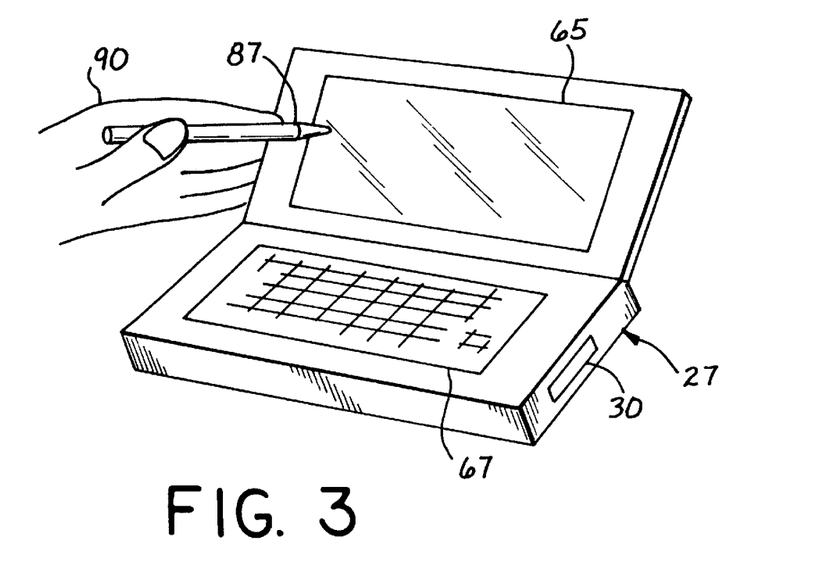
FIG. 3 illustrates a host-personal computer system according to the present invention.

FIG. 3 illustrates a host personal computer 27, according to the presently preferred embodiment. The host personal computer 27 preferably comprises a Personal Digital Assistant (PDA). The host personal computer 27 may comprise any desktop of laptop computer, as well. When the host personal computer 27 comprises a personal digital assistant, as presently preferred, Windows® CE (Pegasus) software is preferably used. This software preferably operates on the Windows® CE operating system. Other commercially available software packages, or customized software packages, may be used with the present invention. A pointing device 87, held by the hand 90 of a user, may be used to input data into the host personal computer 27 via a touch sensitive display 65. The host personal computer 27, having the real-time biological data processing PC card 10 of FIG. 1 inserted therein, is configured into a powerful diagnostic spirometry data collecting and analyzing instrument. Since the real-time biological data processing PC card 10 uses the keyboard 67, display 65, storage 63, microprocessor 61, power supply (not shown), and data transmission and printing capabilities (not shown) of the host computer system 27, the real-time biological data processing PC card 10 itself is very inexpensive and rudimentary in design. Yet, the real-time biological data processing PC card 10 is very powerful. The software loaded within the host personal computer 27 is preferably configured to allow the real-time biological data processing PC card 10 to interface, via PCMCIA format, with any other of a variety of personal computers, such as a desktop personal computer, or a notebook personal computer, for example.

The host personal computer 27 can transmit data via any conventional means, such as a serial port cable or a modem connection through an RJ11 phone plug. Data may be transmitted over the internet, for example. In home disease management, for example, the host personal computer 27 can be configured to gather, process, and transmit additional information on the patient's medication, diet, symptoms, and other parameters. The combination of elements of the present invention thus provides a very portable, lightweight, and inexpensive means for diagnosing and monitoring patients.

Figure 4:
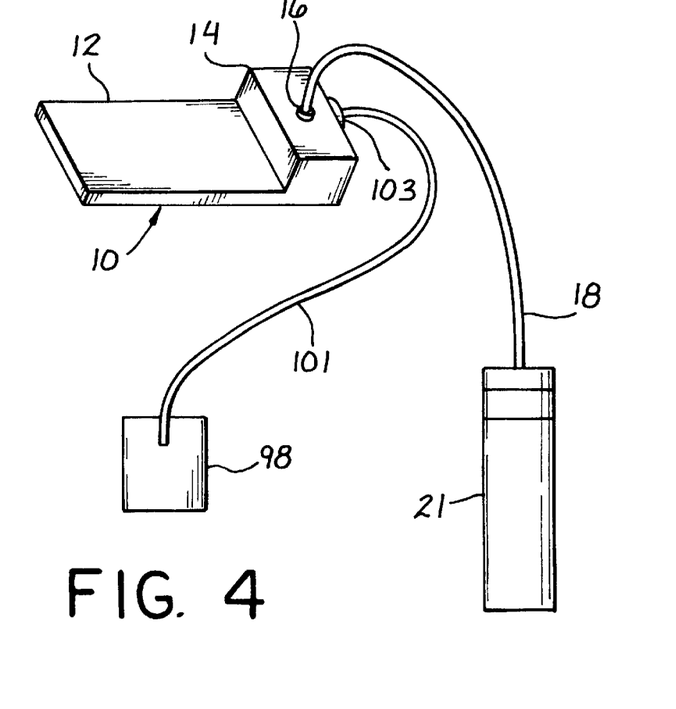
FIG. 4 illustrates a real-time biological data processing PC card according to the presently preferred embodiment.

FIG. 4 illustrates a real-time biological data processing PC card 10, having both a disposable spirometry mouthpiece 21 and a pulse oximeter finger clip 98. Like components are designated with like reference numbers. As with the embodiment of FIG. 1, the disposable spirometry mouthpiece 21 is connected to pressure transducer housing 14 via a flexible air passageway 18 and a pressure input port 16. The pulse oximeter finger clip 98 is connected to the pressure transducer housing 14 via a pulse oximeter cable 101, which transitions into a connector 103.

Figure 5:
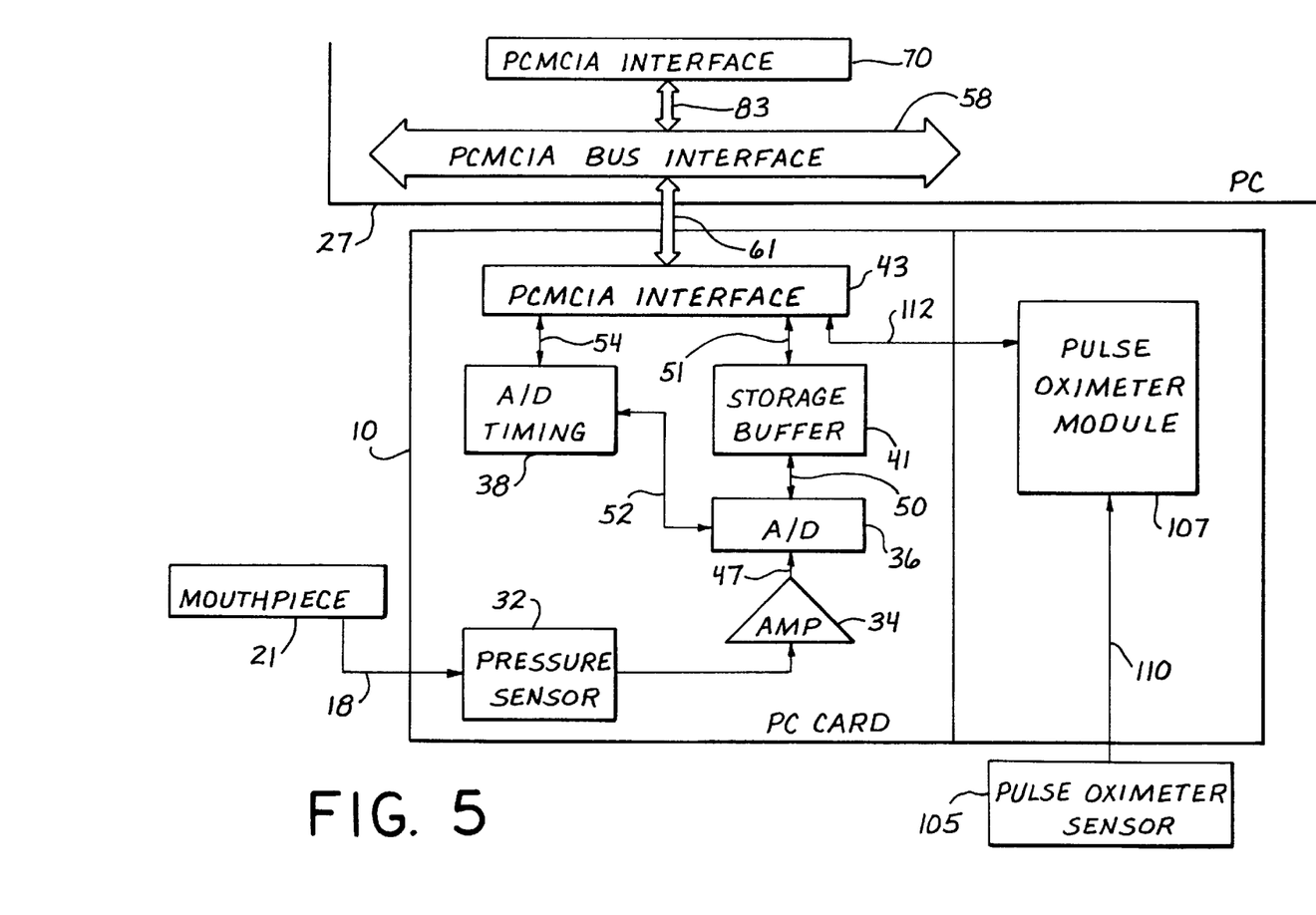
FIG. 5 illustrates a schematic block diagram of the circuitry of the real-time biological data processing PC card according to the presently preferred embodiment.

FIG. 5 illustrates a schematic block diagram of the presently preferred embodiment of FIG. 4. Basically, data from a pulse oximeter sensor 105, such as the pulse oximeter clip 98 (FIG. 4), is fed to a pulse oximeter module 107 via a conductor path 110. As presently embodied, an optical coupler is positioned between the pulse oximeter finger clip 98 and a power source (not shown) connection of the real-time biological data processing PC card 10, to thereby prevent a patient from being shocked therefrom. Data from the pulse oximeter module 107 is then fed to the PCMCIA interface 43 via a conductor path 112. The pulse oximeter module 107 preferably comprises elements similar to the amplifier 34, the analog-to-digital converter 36, the analog-to-digital timing circuit 38, and the storage buffer 41. The elements of the pulse oximeter module 107 may be combined with or into the elements 34, 36, 38, 41 or, as presently embodied, maintained separately therefrom in the pulse oximeter module 107.

As presently embodied, the host personal computer 27 may receive on a real-time basis, process, and monitor spirometry data and pulse oximetry data, either separately of simultaneously. The designation data, in the presently preferred embodiment, indicates to the host personal computer 27 that the real-time biological data processing PC card 10 comprises both spirometry data and pulse oximetry data sensors. The pressure sensor 32 may alternatively be located on the disposable spirometry mouthpiece 21, as can the amplifier 34, the analog-to-digital converter 36, and the analog-to-digital timing circuitry 38, or any combination thereof. Any or all of these elements, in addition to the storage buffer 41, may be positioned on either the disposable spirometry mouthpiece 21, the pulse oximeter sensor 105, or the real-time biological data processing PC card 10, or any combination thereof, or eliminated altogether. Since the present invention is not intended to be limited to PCMCIA interfaces 43, any circuitry capable of forwarding an analog signal to a host personal computer 27 could reduce the need for components within the real-time biological data processing PC card 10. The pulse oximeter sensor 105 and the pulse oximeter module 107 may be manufactured by Nonin® Medical, Inc., located in Plymouth, Minn. According to one embodiment, the pulse oximeter sensor 105 may comprise an 8600 portable pulse oximeter, manufactured by Nonin® Medical, Inc.

Figure 6A:
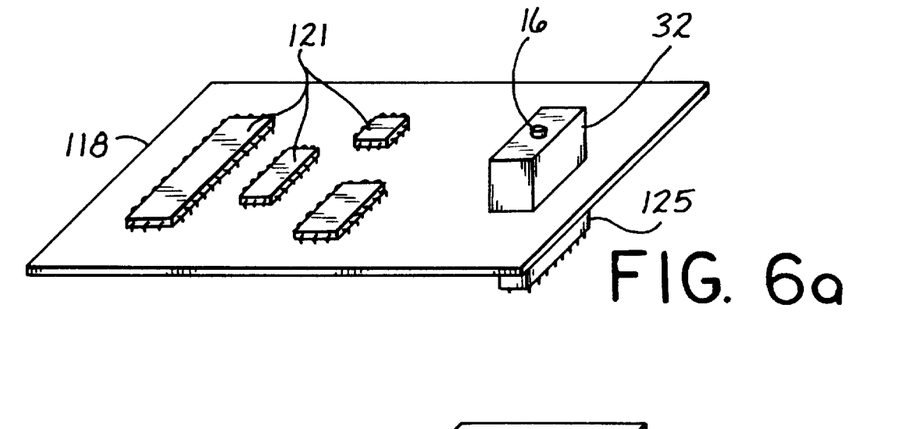
FIG. 6a illustrates a simplified perspective view of the main circuit board of the real-time biological data processing PC card according to the presently preferred embodiment.
Figure 6B:
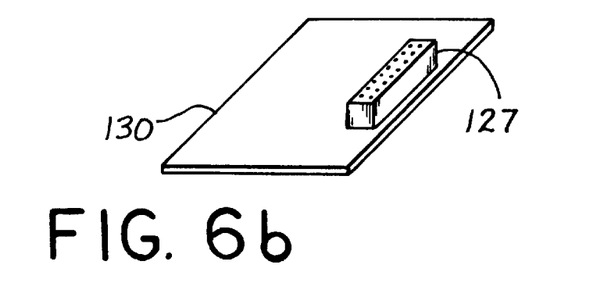
FIG. 6b illustrates a pulse oximeter module circuit board according to the presently preferred embodiment.

FIG. 6a illustrates the main circuit board 118 of the presently preferred embodiment, generally corresponding to the elements 32–54 of FIG. 5. The main circuit board 118 is illustrated comprising a number of IC chips 121, a pressure input port 16, and a pressure sensor 32. A pulse oximetry module connector 125 accommodates a pulse oximetry module connector 127, which is illustrated in FIG. 6b. The pulse oximetry module connector 127 of FIG. 6b is electrically connected to a supplemental circuit board 130. The supplemental circuit board 130 generally corresponds to the pulse oximeter module 107 of FIG. 5.

Figure 7:
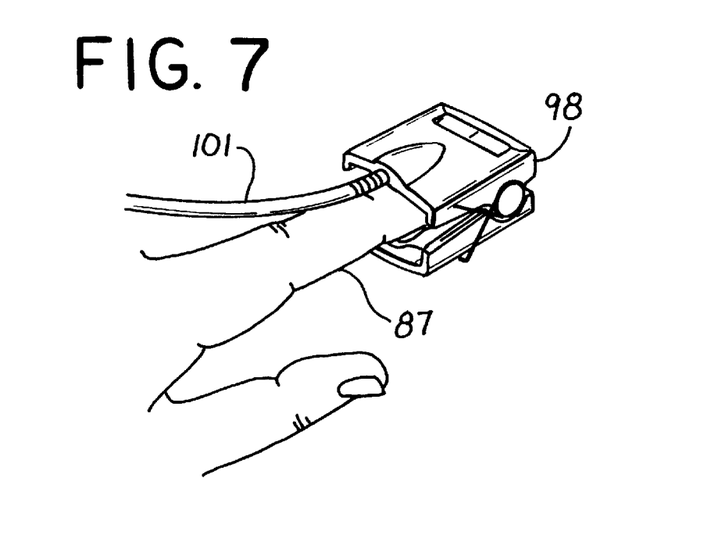
FIG. 7 illustrates an articulated finger clip sensor according to the presently preferred embodiment.

FIG. 7 illustrates a perspective view of a pulse oximeter finger clip 98 connected to a hand 87 of a user. The pulse oximeter finger clip 98 is connected to the supplemental circuit board 130 via a pulse oximeter cable 101.

Although an exemplary embodiment of the invention has been shown and described, many other changes, modifications and substitutions, in addition to those set forth in the above paragraphs, may be made by one having ordinary skill in the art without necessarily departing from the spirit and scope of this invention.

What is claimed is:

1. A portable computer card for collecting biological data, comprising:
  a pressure transducer, the pressure transducer being adapted to receive an air pressure from an air tube and further being adapted to convert the air pressure into an electrical signal;
  an analog-to-digital converter adapted to receive and digitize the electrical signal; and
  a portable computer card interface operatively coupled to the analog-to-digital converter, the portable computer card interface being adapted to provide an interface between the portable computer card and a host microprocessor system.

2. The portable computer card as recited in claim 1, the portable computer card interface comprising a Personal Computer Memory Card International Association (PCMCIA) card interface.

3. The portable computer card as recited in claim 1, further comprising:
  an amplifier adapted to receive and amplify the electrical signal from the pressure transducer, the amplified electrical signal being related to the air pressure; and
  a housing, the pressure transducer, the amplifier, the analog-to-digital converter, and the portable computer card interface being disposed within the housing.

4. The portable computer card as recited in claim 3, further comprising a pressure input port disposed within the housing, the pressure input port being in fluid communication with the pressure transducer and being adapted to receive the air pressure.

5. The portable computer card as recited in claim 4, further comprising a flexible air passageway integrally connected to the housing, the pressure input port being adapted to receive the air pressure via the flexible air passageway.

6. A portable biological data collection device, comprising:
  a portable computer card housing;
  a biological data receiver coupled to the portable computer card housing, the biological data receiver being adapted to receive biological data and to output the biological data;
  signal-conditioning circuitry operatively coupled to the biological data receiver, the signal-conditioning circuitry being adapted to receive the biological data from the biological data receiver and to convert the biological data into digitized biological data; and
  a portable computer card interface disposed within the portable computer card housing, the portable computer card interface being adapted to communicate with a host computer and to relay the digitized biological data to the host computer an a real-time basis as the biological data is converted by the signal conditioning circuitry.

7. The portable biological data collection device as recited in claim 6, the biological data receiver being adapted to receive biological data from a pulse oximetry sensor which is located externally of the portable biological data collection device.

8. The portable biological data collection device as recited in claim 7, the biological data receiver further being adapted to receive biological data from an electrocardiography (ECG) sensor.

9. The portable biological data collection device as recited in claim 6, the biological data receiver being adapted to receive biological data from an ECG sensor.

10. The portable biological data collection device as recited in claim 6, the portable computer card housing having an external surface, and
  the biological data receiver comprising a biological data sensor adapted to be connected to the external surface of the portable computer card housing.

11. The portable biological data collection device as recited in claim 10, the biological data sensor being adapted to output low-amplitude signals on an order of 1 millivolt, and the signal-conditioning circuitry being adapted to output digitized biological data having a resolution greater than 12 bits.

12. The portable biological data collection device as recited in claim 11, the signal-conditioning circuitry being adapted to output digitized biological data which has a resolution of 16 bits.

13. The portable biological data collection device as recited in claim 12, the signal-conditioning circuitry comprising:
   a pressure transducer operatively connected to the biological data sensor;
   an amplifier operatively connected to the pressure transducer; and
   an analog-to-digital converter operatively connected to the amplifier.

14. The portable biological data collection device as recited in claim 10, the biological data sensor being integrally formed onto the external surface of the portable computer card housing.

15. The portable biological data collection device as recited in claim 14, the biological data sensor comprising a spirometer air tube.

16. The portable biological data collection device as recited in claim 6, the portable computer card interface comprising a PCMCIA interface.

17. A host computer configurable among a plurality of biological data collection device modes, comprising:
   a portable computer card slot adapted to receive a portable computer card therein;
   a portable computer card interface adapted to communicate with a portable computer card inserted into the portable computer card slot and adapted to receive digitized biological data from a portable computer card inserted into the portable computer card slot;
   a microprocessor;
   a data bus operatively connected between the microprocessor and the portable computer card interface;
   input means for receiving designation data from a portable computer card within the portable computer card slot, the input means being operatively connected to the microprocessor and the designation data being indicative of a type of the digitized biological data from a portable computer card inserted into the portable computer card slot, the designation data comprising one of a first identifier and a second identifier, the first identifier indicating that the digitized biological data should be interpreted by the microprocessor as spirometer-pressure data and the second identifier indicating that the digitized biological data should be interpreted by the microprocessor as pulse oximetry electrical data; and
   configuring means for configuring the host computer into a real-time spirometer-pressure data collecting and analyzing device upon receipt of the first identifier, and for configuring the host computer into a real-time pulse oximetry electrical data collecting and analyzing device upon receipt of the second identifier, the configuring means being operatively connected to the microprocessor.

18. The host computer as recited in claim 17, the designation data comprising a third identifier indicating that the digitized biological data should be interpreted by the microprocessor as ECG data, and the host computer being configurable into an ECG data collection device mode.

19. The host computer as recited in claim 17, the host computer being configurable among other biological data collection device modes, in addition to a spirometer biological data collection device mode and a pulse oximetry biological data collection device mode.

20. The host computer as recited in claim 17, the input means being adapted for receiving designation data from one of a keyboard and a touch screen display.

21. The host computer as recited in claim 17, the portable computer card slot comprising a PCMCIA card slot.

22. A combination of a plurality of interchangeable biological-data portable computer cards, comprising:
   (a) a spirometer portable computer card, comprising:
      (1) a spirometer portable computer card housing having an external surface;
      (2) a pressure input port disposed within the spirometer portable computer card housing, the pressure input port being adapted to receive an air pressure from an air tube;
      (3) a pressure transducer disposed within the spirometer portable computer card housing, the pressure transducer being adapted to receive an air pressure from an air tube via the pressure input port and to generate an electrical signal, an intensity of the generated electrical signal being proportional to an intensity of the received air pressure;
      (4) an amplifier operatively connected to the pressure transducer, the amplifier being adapted to receive the generated electrical signal and to output an amplified signal;
      (5) an analog-to-digital converter operatively connected to the amplifier, the analog-to-digital converter being adapted to digitize the amplified signal; and
      (6) a portable computer card interface disposed within the spirometer portable computer card housing, the portable computer card interface being adapted to communicate with a host computer and being adapted to relay the digitized amplified signal to the host computer on a real-time basis as the electrical signal is generated from the air pressure; and
   (b) a pulse oximetry portable computer card, comprising:
      (1) a pulse oximetry portable computer card housing having an external surface;
      (2) at least one conductor connected to the pulse oximetry portable computer card housing, the at least one conductor being adapted to collect pulse oximetry data from a patient;
      (3) an analog-to-digital converter operatively connected to the at least one conductor, the analog-to-digital converter being adapted to digitize the amplified signal; and
      (4) a portable computer card interface disposed within the pulse oximetry portable computer card housing, the portable computer card interface being adapted to communicate with a host computer and being adapted to relay the digitized amplified signal to the host computer on a real-time basis as pulse oximetry data is collected from a patient.

23. The combination of a plurality of interchangeable biological-data portable computer cards as recited in claim 22, the spirometer portable computer card being adapted to convert the host computer into a spirometer data collecting and analyzing device, and
   the pulse oximetry portable computer card being adapted to convert the host computer into a pulse oximetry data collecting and analyzing device.

24. The combination of a plurality of interchangeable biological-data portable computer cards as recited in claim 22, further comprising an ECG portable computer card, which comprises:

(1) an ECG portable computer card housing having an external surface;

(2) at least one conductor connected to the ECG portable computer card housing, the at least one conductor being adapted to collect ECG data from a patient;

(3) an amplifier operatively connected to the at least one conductor, the amplifier being adapted to receive the electrical signal and to output an amplified signal;

(4) an analog-to-digital converter operatively connected to the amplifier, the analog-to-digital converter being adapted to digitize the amplified signal; and (5) a portable computer card interface disposed within the ECG portable computer card housing, the portable computer card interface being adapted to communicate with a host computer and being adapted to relay the digitized amplified signal to the host computer on a real-time basis as ECG data is being collected from a patient.

25. A portable computer card for delivering biological data to a host computer, comprising:

a portable computer card housing having an external surface;

at least one conductor connected to the portable computer card housing, the at least one conductor being adapted to collect biological data from a patient; an amplifier operatively connected to the at least one conductor, the amplifier being adapted to receive the biological data and to output an amplified signal;

a power source operatively connected to the amplifier;

insulating means for providing electrical insulation between the power source and the at least one conductor, the insulating means being disposed between the at least one conductor and the amplifier;

an analog-to-digital converter operatively connected to the amplifier, the analog-to-digital converter being adapted to digitize the amplified signal; and a portable computer card interface disposed within the portable computer card housing, the portable computer card interface being adapted to communicate with a host computer and being adapted to relay the digitized amplified signal to the host computer on a real-time basis as biological data is collected from a patient.

26. The portable computer card for delivering biological data to a host computer as recited in claim 25, the insulating means comprising an optical translator, and the power source comprising a conductor for receiving power from a host computer.

* * * * *